US010219917B2

(12) United States Patent
Dewey (10) Patent No.: US 10,219,917 B2
(45) Date of Patent: Mar. 5, 2019

(54) SPINAL IMPLANT INSERTER UTILIZING OFFSET STRIKING ARMS

(71) Applicant: Warsaw Orthopedic, Inc., Warsaw, IN (US)

(72) Inventor: Jonathan M. Dewey, Memphis, TN (US)

( * ) Notice: Subject to any disclaimer, the term of this patent is extended or adjusted under 35 U.S.C. 154(b) by 576 days.

(21) Appl. No.: 14/930,994

(22) Filed: Nov. 3, 2015

(65) Prior Publication Data

US 2017/0119548 A1   May 4, 2017

(51) Int. Cl.
*A61F 2/46* (2006.01)
*A61F 2/44* (2006.01)
*A61B 17/92* (2006.01)

(52) U.S. Cl.
CPC ............ *A61F 2/4611* (2013.01); *A61F 2/442* (2013.01); *A61B 2017/922* (2013.01); *A61F 2002/4681* (2013.01); *A61F 2002/4687* (2013.01); *A61F 2230/0032* (2013.01)

(58) Field of Classification Search
CPC .......... A61F 2/44; A61F 2/442; A61F 2/4455; A61F 2/446; A61F 2/4465; A61F 2/447; A61F 2/4611; A61F 2002/444; A61F 2002/4475; A61F 2002/448; A61F 2002/4485; A61F 2002/449; A61F 2002/4681; A61F 2002/4687
USPC .................................................. 606/99, 100
See application file for complete search history.

(56) References Cited

U.S. PATENT DOCUMENTS

| 7,060,073 | B2 * | 6/2006 | Frey ..................... | A61B 17/025 606/247 |
| 7,481,812 | B2 * | 1/2009 | Frey ..................... | A61B 17/025 606/85 |
| 7,578,820 | B2 * | 8/2009 | Moore ............... | A61B 17/1604 600/203 |
| 7,967,863 | B2 * | 6/2011 | Frey ................... | A61B 17/1604 623/17.11 |
| 8,828,082 | B2 * | 9/2014 | Puno .................. | A61B 17/1757 623/17.16 |
| 9,345,586 | B2 * | 5/2016 | Hunt .................. | A61B 17/1659 |
| 2002/0165550 | A1 * | 11/2002 | Frey ..................... | A61B 17/025 606/85 |
| 2004/0030346 | A1 * | 2/2004 | Frey .................... | A61B 17/1604 606/99 |
| 2005/0049623 | A1 * | 3/2005 | Moore ............... | A61B 17/1604 606/170 |
| 2006/0229627 | A1 * | 10/2006 | Hunt .................. | A61B 17/1659 606/86 R |
| 2006/0264968 | A1 * | 11/2006 | Frey ..................... | A61B 17/025 606/99 |

(Continued)

*Primary Examiner* — Eric S Gibson (57) ABSTRACT

A device for inserting a spinal implant into a disc space between two adjacent vertebrae. An elongated inserter defines a first axis and has an implant securing or clamping device at a distal end, holding the implant. An arcuate striking arm is pivotally connected at one end to the inserter. A slap hammer has a shaft. The second end of the striking arm is connected to the slap hammer. A force applied to the slap hammer defines an axis of force, moving the slap hammer shaft along the axis of force. The striking arm moves and pivots with respect to the inserter. The motion of the striking arm translates motion to the inserter and to the implant clamping device. An otherwise offset axis of the implant aligns with a desired direction of travel into the disc space.

20 Claims, 10 Drawing Sheets

(56) References Cited

U.S. PATENT DOCUMENTS

| | | | |
|---|---|---|---|
| 2007/0093850 A1* | 4/2007 | Harris | A61F 2/4611 606/99 |
| 2008/0306489 A1* | 12/2008 | Altarac | A61F 2/4611 606/99 |
| 2008/0306557 A1* | 12/2008 | Altarac | A61F 2/4611 606/86 A |
| 2009/0270873 A1* | 10/2009 | Fabian | A61F 2/442 606/99 |
| 2009/0312763 A1* | 12/2009 | McCormack | A61B 17/025 606/83 |
| 2011/0009969 A1* | 1/2011 | Puno | A61B 17/1757 623/17.12 |
| 2011/0230970 A1* | 9/2011 | Lynn | A61F 2/442 623/17.16 |
| 2012/0226357 A1* | 9/2012 | Varela | A61F 2/447 623/17.16 |
| 2015/0045892 A1* | 2/2015 | Lynn | A61F 2/447 623/17.16 |
| 2015/0297247 A1* | 10/2015 | Seex | A61F 2/4684 623/17.11 |
| 2016/0228170 A1* | 8/2016 | Malcolmson | A61F 2/4611 |
| 2017/0100260 A1* | 4/2017 | Duffield | A61F 2/4611 |
| 2017/0119548 A1* | 5/2017 | Dewey | A61F 2/4611 |
| 2017/0156879 A1* | 6/2017 | Janowski | A61F 2/447 |
| 2018/0140438 A1* | 5/2018 | Robinson | A61F 2/4603 |

* cited by examiner

FIG. 15

SPINAL IMPLANT INSERTER UTILIZING OFFSET STRIKING ARMS

BACKGROUND OF THE INVENTION

Field of the Invention

The present invention relates to an apparatus for inserting a spinal implant into a disc space between two vertebral bodies, including an upper vertebral body, and a lower vertebral body in a patient, and a method for inserting the implant. More particularly, the present invention relates to an apparatus for inserting a spinal implant into a desired implant location between respective posterior rims of two adjacent vertebral bodies, the adjacent vertebral bodies defining a disc space in a patient, and a method for inserting the implant into the desired implant location, preferably using a lateral approach to the disc space.

Description of the Prior Art

Spinal implants, configured for insertion into a patient's disc space between two adjacent vertebral bodies are known. A posterior approach, or an anterior approach, to the disc space are relatively complex invasive surgeries, involving discomfort, and a relatively long recovery time for the patient.

A posterior lateral or lateral approach into a disc space is relatively less invasive. The lateral approach, however, is complicated by the configuration of the adjacent vertebral bodies themselves, particularly the posterior portions thereof. For example, the posterior portion of each vertebral body defines a posterior rim. The posterior rim includes numerous adjacent projecting bony prominences, for example, at least two pedicles, two laminae, and several processes, including transverse processes and a posterior spinous process. These bones also define a vertebral foramen, through which the spinal cord passes. A lateral insertion of the spinal implant into the disc space, using traditional spinal implants, traditional insertion tools, and traditional lateral approach techniques, often results in interference between the implant or the tool and at least one of these bony prominences adjacent the posterior rims of the adjacent vertebral bodies.

In addition, the lateral insertion pathway to insert the implant into the disc space using traditional implant insertion tools may not facilitate satisfactory control of the implant. In particular, traditional insertion tools often result in an approach to a position proximate the disc space wherein an axis defined through the implant is offset from a desired insertion path into the disc space.

SUMMARY OF THE INVENTION

It is an object of the present invention to provide a spinal implant insertion apparatus and method of insertion, which substantially obviates one or more of the shortcomings experienced with the prior art.

It is another object of one embodiment of the present invention to provide a spinal implant insertion apparatus for inserting an implant into a desired implant location between posterior rims of two adjacent vertebral bodies, the two adjacent vertebral bodies defining a disc space of a patient. The apparatus includes an elongated inserter having a proximal end and a distal end, a non-movable portion extending from the proximal end to the distal end, and a movable portion extending from the distal end to an intermediate position intermediate the distal end and the proximal end, the movable portion being movably engaged with the non-movable portion proximate the intermediate position. A securing or clamping device, configured to secure or clamp the implant, is defined at the distal end. The implant, when clamped in the implant holder, and positioned proximate the desired implant location following a posterior lateral or lateral approach to the disc space, defines an axis which may be offset from a desired path of travel into the desired implant location. The apparatus also includes a striking arm, having two ends, a first end being attached to the inserter, and a second end defining a retention mechanism, in the form of a stem and a spherical ball. The apparatus also includes a slap hammer. The slap hammer includes a shaft having a proximal end and a distal end, with an attachment portion defined at the distal end, configured to engage the retention mechanism on the striking arm, a slap handle defined at the proximal end, and a weight mounted on the shaft therebetween.

It is a further of another embodiment object of the present invention to provide a spinal implant insertion apparatus wherein slapping the slap hammer defines a force, the force moving the slap hammer shaft and the attachment portion. The second end of the striking arm is moved in the direction of the force due to the retention mechanism of the striking arm being mounted in the attachment portion of the slap hammer. The first end of the striking arm moves in correspondence with the second end, imparting a translational motion to the inserter, and in turn to the implant holder. The translational motion results in the implant holder and the implant moving in the desired direction of travel into the desired implant location. Having been properly aligned, the implant can be moved into the desired implant location without interfering with the bony prominences proximate the posterior rims of the adjacent vertebral bodies.

It is a further object of yet another embodiment of the invention to provide a method of inserting a spinal implant into a desired implant location between posterior rims of two adjacent vertebral bodies, the adjacent vertebral bodies defining a disc space of a patient. The method includes utilizing the spinal implant insertion apparatus described above. The method includes preparing the patient's disc space, clamping the implant with the clamping device, moving the implant holder and the implant to a pre-implantation position either proximate the disc space, or within the disc space, preferably using a lateral approach to a pre-implantation position within the disc space, wherein the axis of the implant may be offset from a desired path of travel into the desired implant position, positioning the slap hammer in a position proximate disc space and aligned with the desired path of travel, attaching the connector on the striking arm to the attachment portion of the slap hammer, applying a force to the slap hammer, the force moving the retention mechanism and the attachment portion in the direction of the force, thereby moving the second end of the striking arm with respect to the shaft of the slap hammer, correspondingly moving the first end of the striking arm with respect to the inserter, and translating motion from the striking arm to the inserter and the clamping device, the translation of the motion to the clamping device aligning the axis of the implant with the desired path of travel into the desired implantation location.

It is a further object of a further embodiment of the invention, to provide a spinal implant insertion apparatus and method which inserts a B-shaped implant, from the pre-implantation position proximate the disc space, the pre-implantation position being located within the disc space, after using a lateral approach to the disc space, and into the desired implantation position, without interfering with any of the prominent bones proximate the posterior rims of the adjacent vertebral bodies.

These and other objects of the present invention will be apparent from review of the following specification and the accompanying drawings.

DETAILED DESCRIPTION OF THE PREFERRED EMBODIMENT

In accordance with one embodiment of the invention, and as broadly embodied in FIGS. 1-14, provided is a spinal implant insertion apparatus 10. In this embodiment, spinal implant insertion apparatus 10 includes an elongated inserter 20. As depicted in FIGS. 3-8, the elongated inserter 20 includes a proximal end 22, and a distal end 24. A non-movable portion 26 extends from the proximal end 22 to the distal end 24. A movable portion 30 extends from the distal end 24 to an intermediate position 28 intermediate the proximal end 22 and the distal end 24. A post 32 extends from the non-movable portion 26. The movable portion 30 includes an edge 34, configured to move in a track 36 defined in the non-movable portion 26. The movable portion 30 also includes a first threaded portion 38 on the external surface thereof. A tightening knob 40, having a second threaded portion 42 on an internal surface thereof, is provided over the first threaded portion 38 on the surface of the movable portion 30. As the tightening knob 40 is rotated either clockwise or counter-clockwise, the threads of the second threaded portion 42 engage with, and rotate on, the threads of the first threaded portion 38, which causes the movable portion 30 to move, either in the direction of the proximal end 22 or in the direction of the distal end 24, depending on the direction of rotation.

Figure 1:
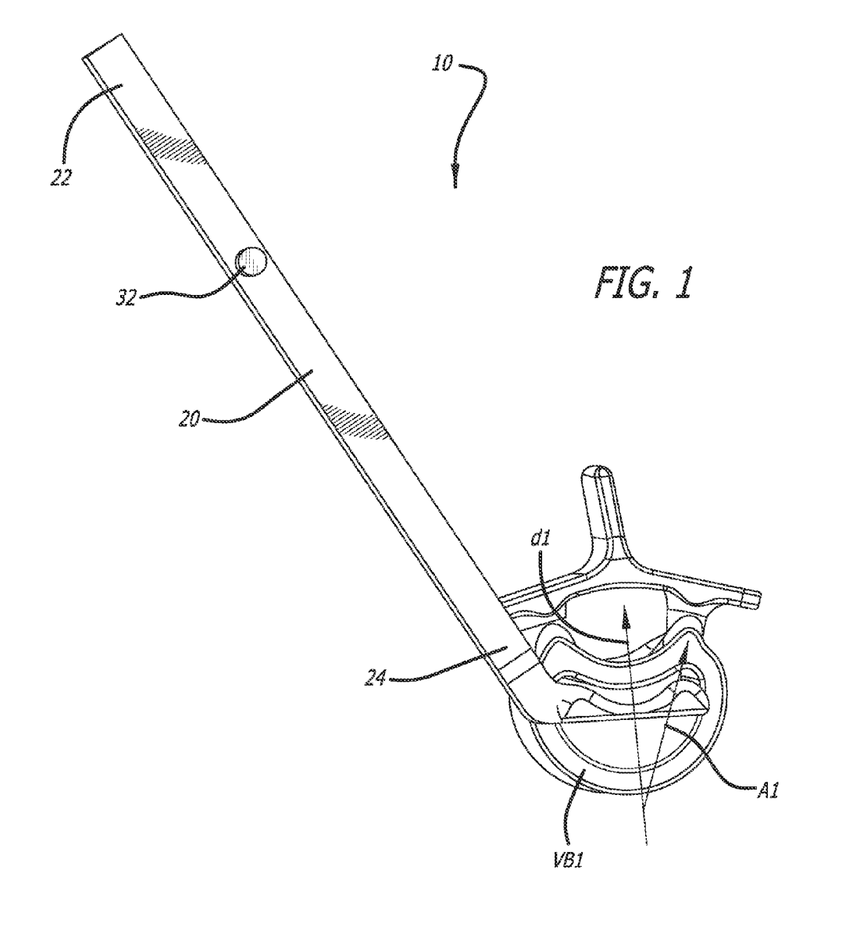
FIG. 1 is an upper perspective view of an elongated inserter, and an implant connected to the inserter in accordance with a preferred embodiment of the present invention.
Figure 2:
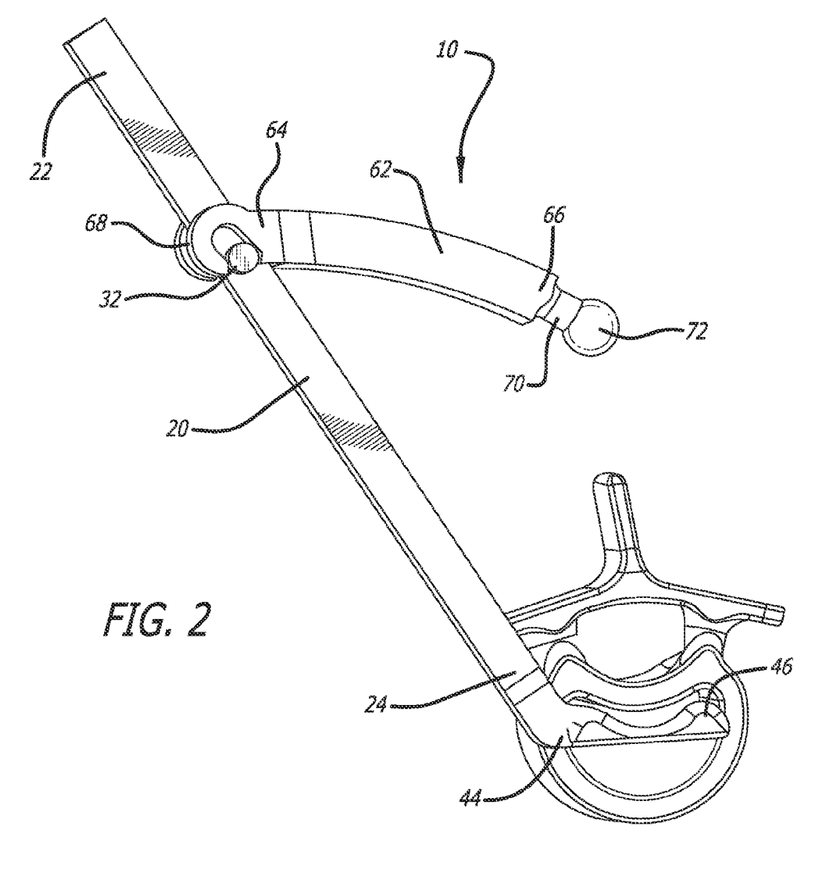
FIG. 2 is an upper perspective view of the elongated inserter, the implant connected to the inserter, and a striking arm in accordance with a preferred embodiment of the present invention.
Figures 3, 4:
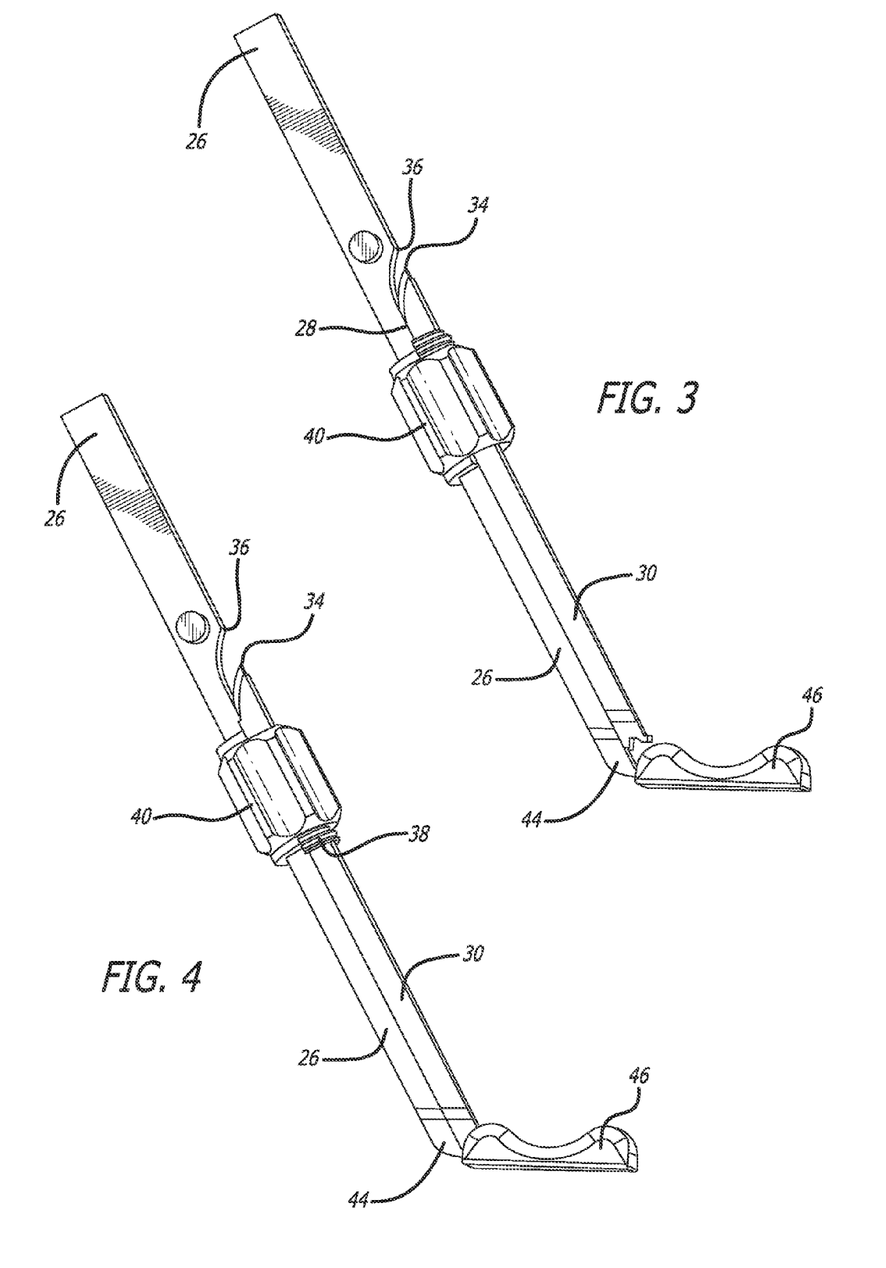
FIG. 3 is an upper perspective view of the elongated inserter, having a movable portion, a non-movable portion, and a first preferred embodiment of a connector for connecting the elongated inserter to a first preferred embodiment of an implant, in accordance with the present invention.
FIG. 4 is an upper perspective view of the elongated inserter of FIG. 3, with the first preferred embodiment of the connector connected to the first preferred embodiment of the implant in accordance with the present invention.
Figure 5:
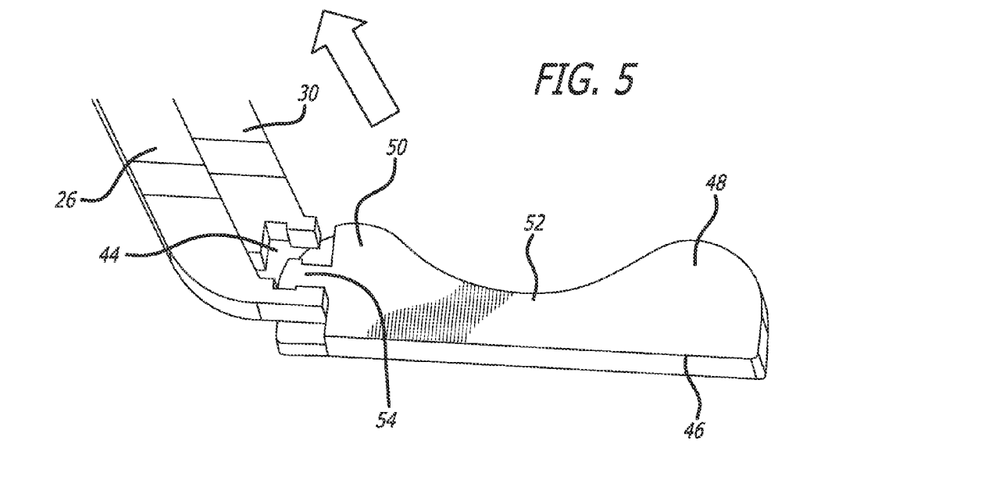
FIG. 5 is an upper perspective view depicting the first preferred embodiment of the connector, and the first preferred embodiment of the implant, in the released position.
Figure 6:
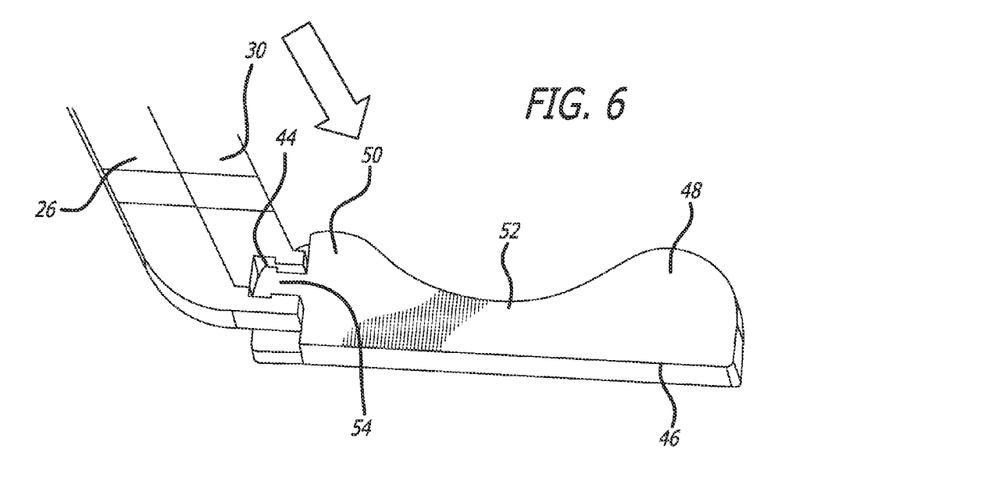
FIG. 6 is an upper perspective view depicting the first preferred embodiment of the connector, and the first preferred embodiment of the implant, in the clamped position.
Figure 7:
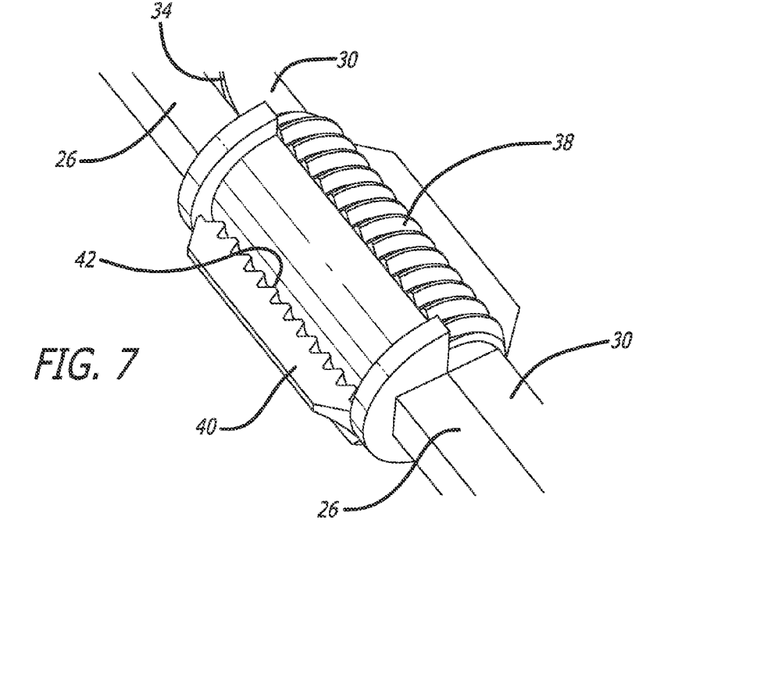
FIG. 7 is an upper perspective view of a portion of the embodiment of the elongated inserter depicted in FIG. 3.
Figure 8:
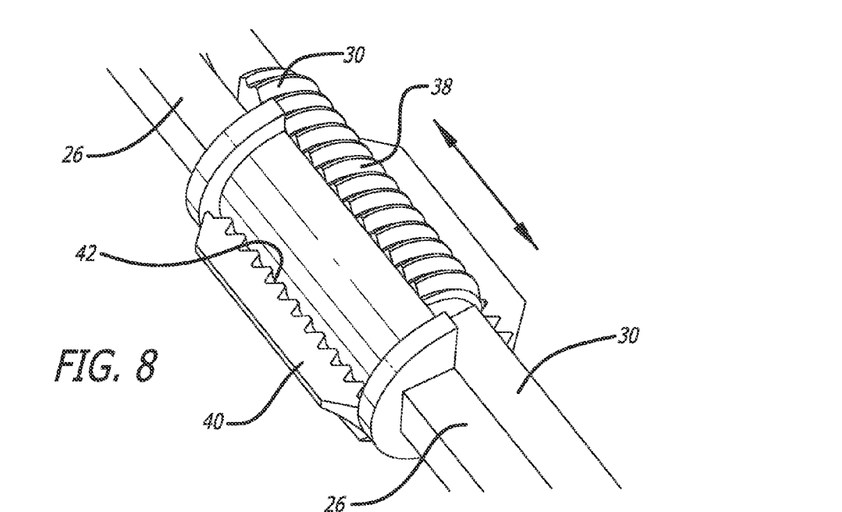
FIG. 8 is an upper perspective view depicting operation of the portion of the embodiment of the elongated inserter depicted in FIG. 7.

The distal end 24 of the inserter 20 further includes a clamping device 44, configured to clamp a spinal implant 46. Spinal implant 46 preferably is configured for posterior lateral or lateral insertion to a pre-implantation position proximate a disc space, the disc space having been prepared earlier for receipt of the implant 46 in a desired implantation position between posterior rims of adjacent vertebral bodies, the adjacent vertebral bodies defining the disc space (in the drawings, only one vertebral body, the lower vertebral body VB 1, and its respective posterior rim PR1, are shown). As depicted in FIGS. 5 and 6, a suitable spinal implant 46, a B-shaped spinal implant is configured for insertion into the desired implantation position with minimal or no interference between the implant 46 and the projecting bony prominences in the posterior rims of the vertebral bodies which define the disc space. This embodiment of spinal implant 46 includes a projecting lobe 48, a partial lobe 50, a concave recess 52, and an attachment portion 54, configured to be clamped by the clamping device 44 on the distal end 24 of the inserter 20. As depicted in FIGS. 5 and 6, this embodiment of the attachment portion 54 has a T-shape, and the clamping device has an inverse T-shape, but the invention is not limited to this configuration. This feature has the purpose of allowing manipulation of the implant without it becoming detached from the inserter. Referring to FIG. 6, when rotation of the tightening knob 40 causes the movable portion 30 to move toward the distal end 24, the clamping device 44 engages the attachment portion 54 of the implant 46. Alternatively, referring to FIG. 5, when rotation of the tightening knob 40 causes the movable portion 30 to move toward the proximal end 22, the clamping device 44 disengages from the attachment portion 54 of the implant 46.

Another suitable spinal implant 46, also a B-shaped implant, is disclosed in U.S. Patent Application No. [Medtronic Ref. No. C0001564.USU1; M&F Ref. No.

Figures 9, 10:
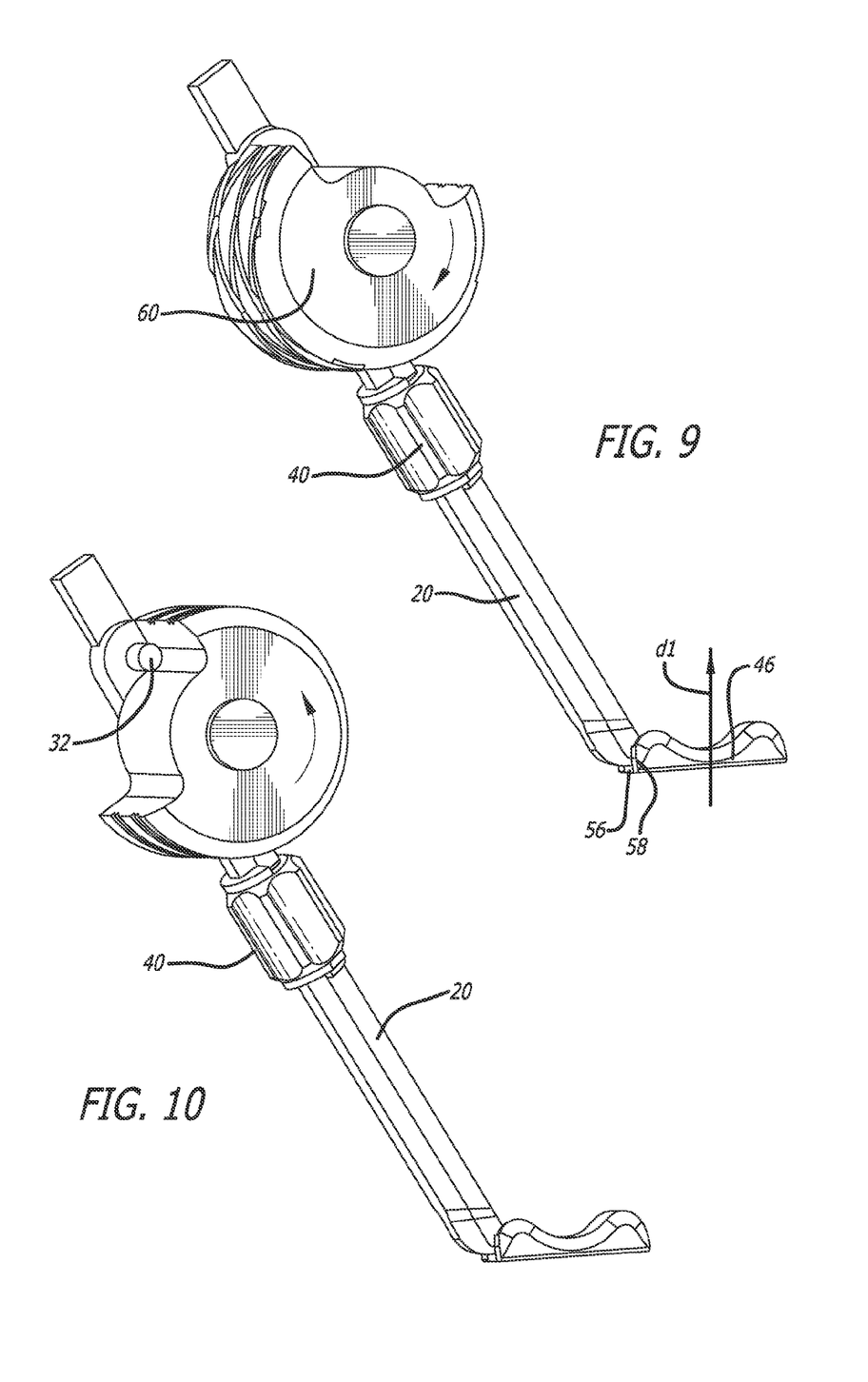
FIG. 9 is an upper perspective view of the elongated inserter, having a second preferred embodiment for connecting the elongated inserter to a second preferred embodiment of an implant, and for imparting movement to the implant with a weighted wheel illustrated in an impact or strike position.
FIG. 10 is an upper perspective view of the elongated inserter of FIG. 9, with the second preferred embodiment connected to the second preferred embodiment of the implant, and illustrating the weighted wheel being returned to its pre-strike position.
Figure 11:
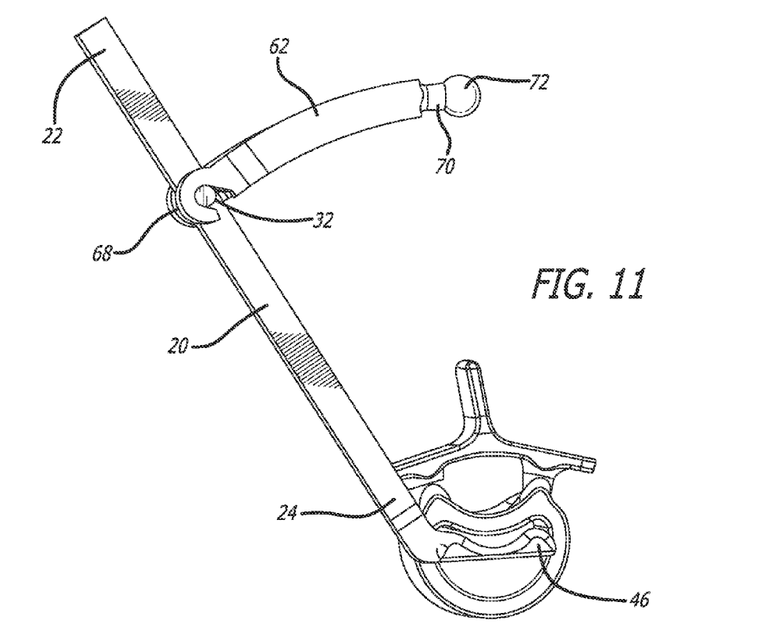
FIG. 11 is an upper perspective view of the elongated inserter, the implant connected to the inserter, and the striking arm pivotally connected to the inserter, in accordance with a preferred embodiment of the present invention.
Figure 12:
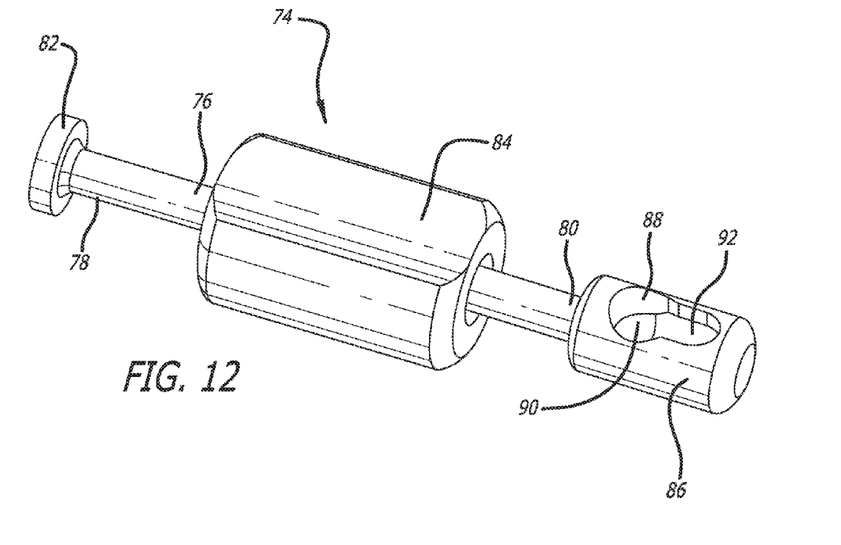
FIG. 12 is an upper perspective view of a slap hammer device in the implant insertion apparatus in accordance with the present invention.

102.0084-00000], filed on [Date], the contents of which are incorporated herein by reference. This embodiment of a spinal implant 46 is depicted broadly in FIGS. 9 and 10, with another embodiment of a clamping device 44. In this embodiment, a slot 56 has been defined in one end of the implant 46, and a corresponding cam or clamp 58 has been added to the distal end 24 of the inserter 20. In addition, as depicted in FIGS. 9 and 10, a weighted wheel 60 has been rotatably mounted on the inserter 20, intermediate the proximal end 22 and the tightening knob 40. Weighted wheel 60 also can be rotatably mounted on a plate (not shown), which can be connected to the inserter 20. As depicted in FIG. 9, when the weighted wheel 60 is rotated, it strikes post 32, creating a moment, which moves the implant 46 posteriorly in a desired path of travel d1. FIG. 10 depicts the weighted wheel 60 being returned to its pre-strike position so that it can be rotated to impart movement to the implant along the desired path d via striking post 32 shown in FIG. 9.

Although each of the implants 46 described above and depicted in the drawings are B-shaped, the invention is not limited to use with a B-shaped implant. Also, the implant is shown clamped laterally, but it is contemplated that the implant could be clamped anywhere.

While the implant 46 is clamped by the clamping device 44, an axis A1 is defined through the implant 46. In some cases, the axis A1 may be offset from the desired path of travel d1 into the desired implantation position between the posterior rims of the adjacent vertebral bodies. If left uncorrected, this offset axis A1 potentially could cause, upon an attempted insertion of the implant into the desired implantation position, possible undesirable interference between the implant and the projecting bony prominences of the posterior rims of the adjacent vertebral bodies.

As embodied in FIGS. 2 and 11-14, an arcuate striking arm 62 includes a first end 64 and a second end 66. The first end 64 defines a hook 68. Hook 68 is configured to engage the post 32 on inserter 20. The second end 66 of the striking arm 62 defines a stem 70, which connects to a spherical ball 72. It is understood that a plurality of connection mechanisms could be employed to facilitate easy removal (the possibility of a detent that would require overcoming), or more intentional removal (a threaded connection or a connection that would require depressing a button to release, etc). A ball was depicted to allow a pure translational force to be transmitted through the system, without other moments being transferred. A ball and socket connection would also allow the slap hammer to be used in a plurality of angles relative to the inserter and striking arm, though this freedom of movement could be restricted to give the desired force transfer.

As embodied in FIGS. 11-14, a slap hammer 74 includes a shaft 76. Shaft 76 of slap hammer 74 has a posterior end 78 and a distal end 80. A slap handle 82 is defined at the posterior end 78 of the shaft 76. A weight 84 is slidably mounted on the shaft 76 intermediate the posterior end 78 and the distal end 80. An attachment portion 86, preferably a lock-nut, is defined at the distal end 80 of the shaft 76. Attachment portion 86 includes a laterally-facing opening 88. The laterally-facing opening 88 includes a round opening portion 90 communicating with a narrow slot portion 92. The round opening 90 is configured to pass both the spherical ball 72 and the stem 70 of the striking arm 62 therethrough. The slot portion 92 is configured to receive the spherical ball 72 and the stem 70 therein, and to lock them in place in the attachment portion 86.

Figure 13:
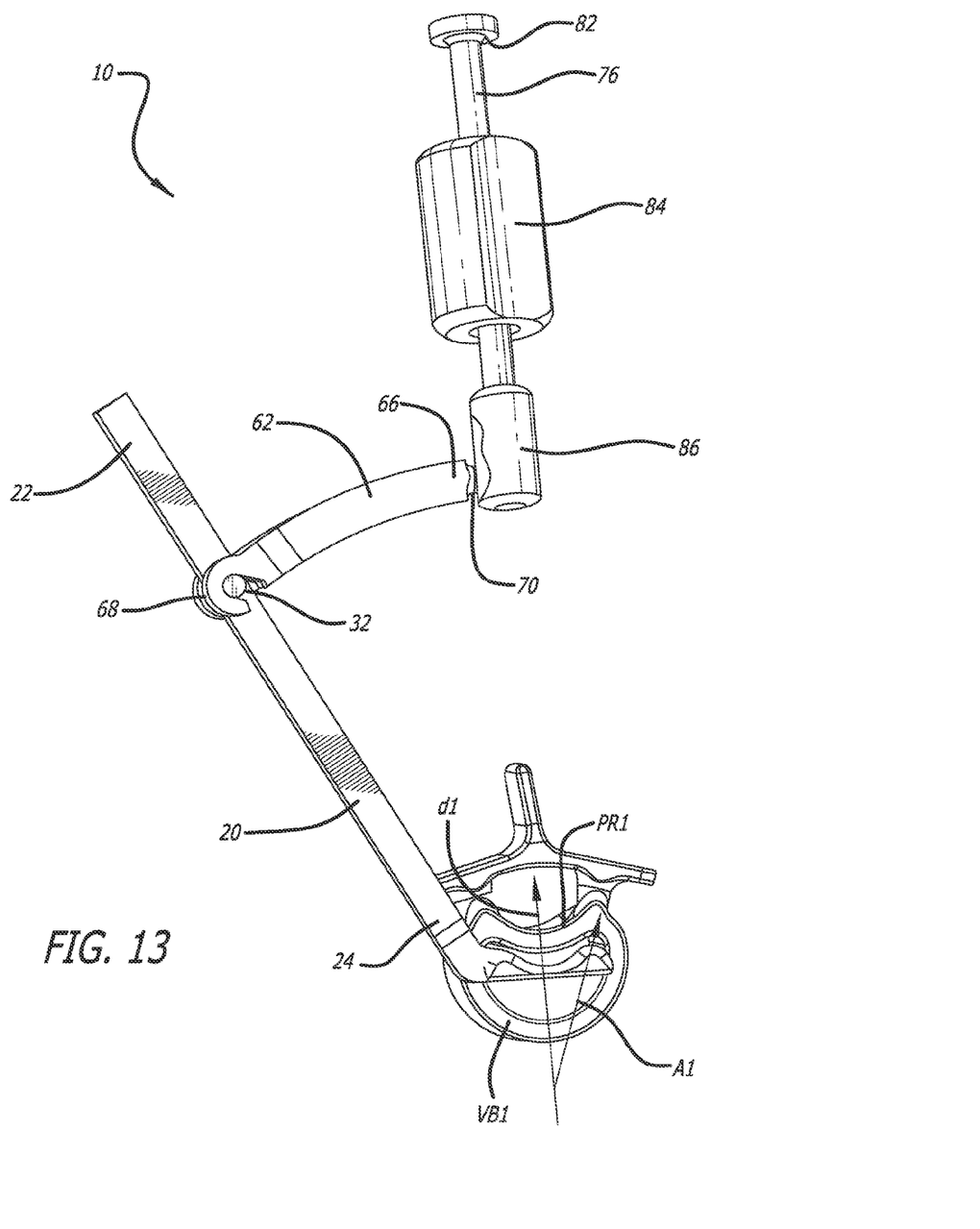
FIG. 13 is a side view of the elongated inserter, the implant connected to the inserter, and the striking arm pivotally connected to the inserter and to the slap hammer device, in accordance with a preferred embodiment of the present invention.
Figure 14:
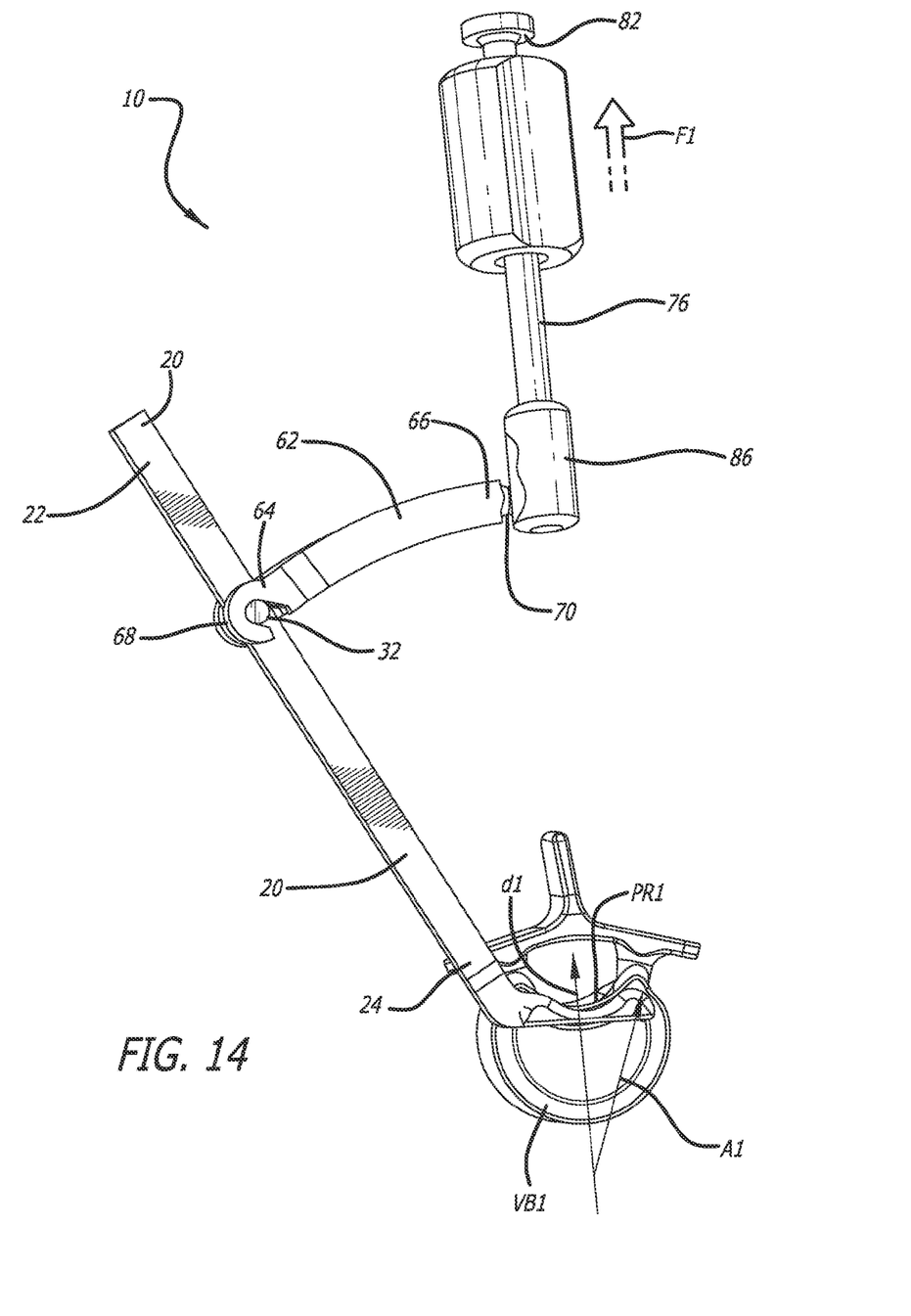
FIG. 14 is a side view of the embodiment of the invention depicted in FIGS. 11-13, depicting operation of one embodiment of the spinal implant insertion apparatus.

A method of inserting the implant 46 into the disc space, as broadly depicted in FIGS. 1-14, is as follows. The patient's disc space is prepared. The implant 46 is clamped by the clamping device 44, and moved, preferably via a posterior lateral or lateral approach, to a pre-implantation position which can be proximate the disc space, or preferably within the disc space following the posterior lateral or lateral approach thereto. The slap hammer 74 is positioned proximate the disc space, with the shaft 76 aligned with the desired path of travel d1. The hook 68 at the first end 64 of the striking arm 62 is hooked to the post 32 on the inserter 20. The stem 70 and spherical ball 72 on the second end 66 of the striking arm 62 are locked into place in the opening 88 of the attachment portion 86 of the slap hammer 74. A force f1 is applied to the slap hammer 74. As depicted in FIGS. 13 and 14, the force f1 applied to the slap hammer 74 acts on the components of the slap hammer 74, causing slap hammer shaft 76 to move in a direction of the force f1 away from the disc space. As the shaft 76 moves, the attachment portion 86, the stem 70, and the spherical ball 72, all also move in the direction of the force f1. The slap handle 82 defines the limit of travel of the slap hammer 74. Movement of the stem 70 and the spherical ball 72 in the direction of the force f1 also moves the second end 66 of the striking arm 62, to which it is attached, in the direction of the force f1, correspondingly moving the first end 64 of the striking arm 62. Motion of the first end 64 causes the hook 68 at the first end 64 of the striking arm 62, which is hooked to the post 32, to impart a translational motion to the inserter 20 and to the implant clamping device 44. The translational motion results in the offset axis A1 of the implant 46 to move toward the direction of the axis of force f1, and thereby into the desired path of travel d1.

While the apparatus best shown in FIGS. 3-8 and 11-14 has been described in association with the above method, other insertion apparatuses permitting the needed force transfer through the insertion apparatus to the implant are contemplated herein. By way of example, the above method could be modified to permit the insertion apparatus of FIGS. 9 and 10 using the rotational weighted wheel configuration to apply a moment to the system instead of the slap hammer.

In accordance with the principles of the invention, the implant 46 now is oriented properly to be moved into the desired implantation position. The implant 46 can be inserted into the desired implantation position without interfering with the bony prominences at the respective posterior rims of either one of the adjacent vertebral bodies.

Figure 15:
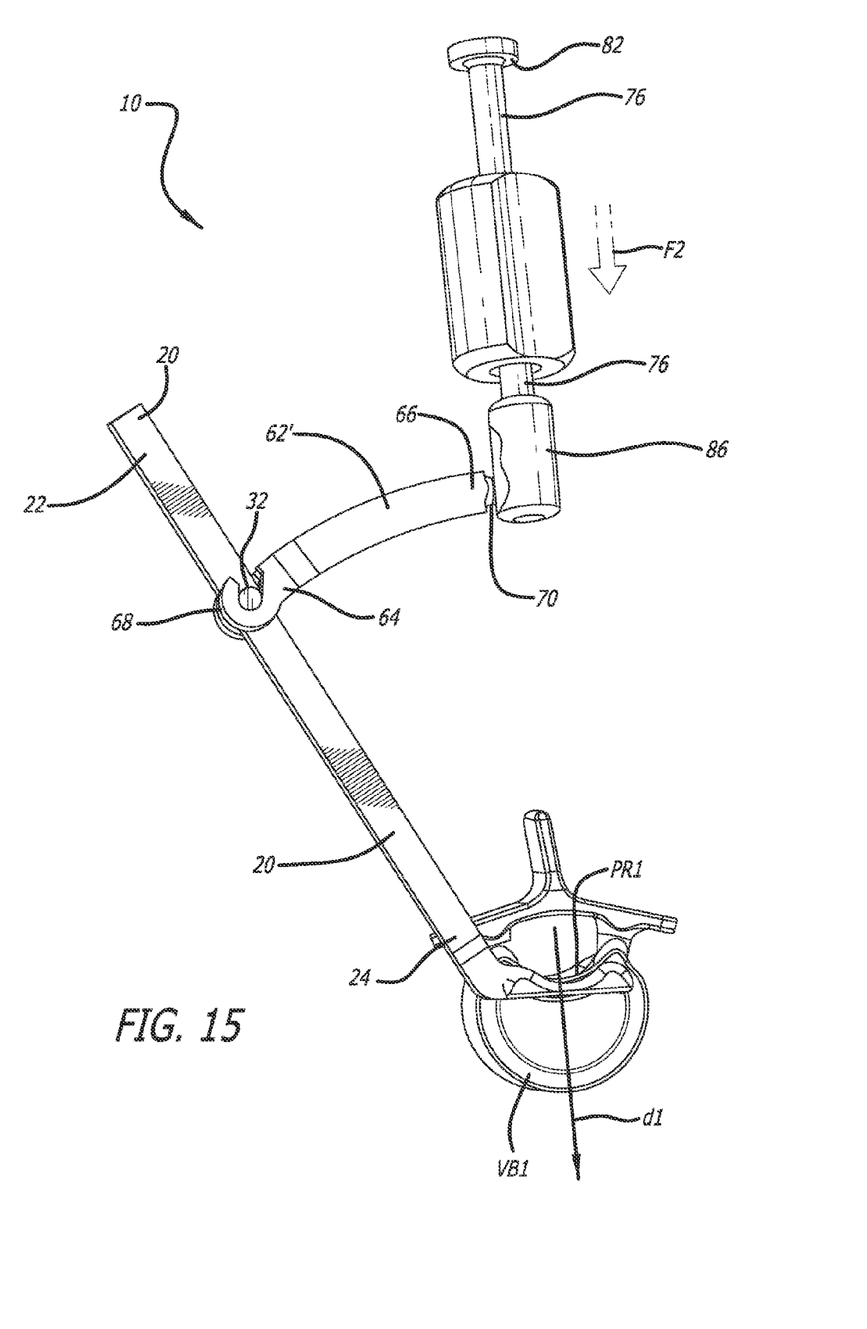
FIG. 15 is a side view of an embodiment of the invention, depicting operation of the slap hammer to impart an impact force to move one embodiment of the spinal implant insertion apparatus anteriorly.

As embodied in FIG. 15, an alternative embodiment of the insertion apparatus varies from the insertion apparatus of FIGS. 11-14 in that the arcuate striking arm 62 includes a hook 68 configured to engage the post 32 on inserter 20 in a direction opposite to that illustrated in FIGS. 11-14. This change of configuration permits the weight slidably mounted on the shaft 76 intermediate the posterior end 78 and the distal end 80 to apply a force F2 in the direction shown by the corresponding arrow to move the implant anteriorly. Although this embodiment of the insertion apparatus is being illustrated with a B-shaped implant it can be used with any other shaped implant and this apparatus may be particularly useful to drive a TLIF implant, such as the Cresent™ available from Medtronic, in the anterior direction. This also could be utilized for rotating and placing a laterally placed implant to a purely A/P orientation. Using rotational and translational movements could give the surgeon a plurality of possible, complex or compound movements.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. For example, and not by way of limitation, the striking arm 62 could be manufactured integral with the inserter 20. In addition, the striking arm 62 could be configured to apply a force at any direction to any interbody device wherein the insertion pathway differs from the direction of desired movement. The offset striking arm 62 also could be configured to convert moments/rotation into translation, moments at one location into a moment at another location, and translations into moments. In addition, additional pivot points could be established to provide the surgeon with more complex movements through a remote striking point. While the implantation space for one embodiment of the implant described herein is for insertion between two adjacent vertebral bodies after removal of at least a portion of the disc there between, it is appreciated that the apparatus and method disclosed herein may be used for a corpectomy procedure wherein the implantation space is formed by removing at least an intermediate vertebral body.

I claim:

1. A spinal implant and an implant insertion apparatus for inserting the spinal implant into a desired implantation position between two adjacent vertebral bodies, the two adjacent vertebral bodies defining a disc space of a patient, the spinal implant and the apparatus comprising:
    a spinal implant defining an axis therethrough; and
    an implant insertion apparatus comprising:
        an elongated inserter, the inserter including a proximal end, an opposite distal end, a non-movable portion extending from the distal end to the proximal end, and a movable portion extending from the distal end to an intermediate position intermediate the proximal end and the distal end, the movable portion and the non-movable portion being movably engaged to one another proximate the intermediate position;
        an implant securing device defined at the distal end, the implant securing device being configured to secure the spinal implant to the inserter, the axis of the spinal implant being offset from a desired path of travel into the desired implantation position while the spinal implant is secured in the securing device and positioned in a pre-implantation position, the pre-implantation position being one of proximate the disc space and within the disc space;
        a striking arm, the striking arm having a first end and a second end, one of the first and second ends being attached to the inserter, the other of the first and second ends defining a connector; and
        a slap hammer, the slap hammer including a shaft, the shaft having a proximal end and a distal end, an attachment portion defined at the distal end, the attachment portion configured to engage the connector on the striking arm;
    wherein application of a force to the slap hammer moves the slap hammer shaft in a direction substantially corresponding to the desired path of travel, the force being translated via the striking arm and the inserter to the spinal implant, thereby moving the axis of the spinal implant into the desired path of travel.

2. The spinal implant and the apparatus as recited in claim 1, wherein the first end of the striking arm includes at least one hook, the at least one hook being configured to engage a post defined on the inserter.

3. The spinal implant and the apparatus as recited in claim 1, wherein the connector on the second end of the striking arm includes a substantially spherical ball.

4. The spinal implant and the apparatus as recited in claim 3, wherein the attachment portion on the slap hammer is configured to engage the substantially spherical ball.

5. The spinal implant and the apparatus as recited in claim 1, wherein the striking arm has a substantially arcuate configuration between the first end and the second end.

6. The spinal implant and the apparatus as recited in claim 1, wherein the movable portion includes a first threaded portion defined on an external surface thereof, the first threaded portion being defined proximate the intermediate position.

7. The spinal implant and the apparatus as recited in claim 6, further comprising a tightening knob provided over the first threaded portion of the movable portion, the tightening knob including a second threaded portion, the second threaded portion engaging the first threaded portion, wherein rotation of the tightening knob moves the movable portion of the inserter relative to the non-movable portion.

8. The spinal implant and the apparatus as recited in claim 1, wherein the implant securing device includes a projecting portion having a selected shape, and the implant has a receiving portion having an inverse shape of the selected shape, the inverse-shaped receiving portion being configured to receive the selected-shaped projecting portion therein.

9. The spinal implant and the apparatus as recited in claim 1, wherein the implant securing device includes a first cam defined at the distal end of the inserter, the first cam being configured to fit into a corresponding slot in the implant.

10. The spinal implant and the apparatus as recited in claim 1, wherein the spinal implant is substantially B-shaped.

11. An implant insertion apparatus for inserting a spinal implant into a desired implantation position between two adjacent vertebral bodies, the two adjacent vertebral bodies defining a disc space of a patient, the implant insertion apparatus comprising:
    an elongated inserter, the inserter including a proximal end, an opposite distal end, a non-movable portion extending from the distal end to the proximal end, and a movable portion extending from the distal end to an intermediate position intermediate the proximal end and the distal end, the movable portion and the non-movable portion being movably engaged to one another proximate the intermediate position;
    a securing device defined at the distal end, the securing device being configured to secure a spinal implant to the inserter;
    a striking arm, the striking arm having a first end and a second end, one of the first and second ends being attached to the inserter, the other of the first and second ends defining a connector; and
    a slap hammer, the slap hammer including a shaft, the shaft having a proximal end and a distal end, an attachment portion defined at the distal end, the attachment portion configured to engage the connector on the striking arm;
    wherein application of a force to the slap hammer moves the slap hammer shaft in a first direction and causes the force to be translated to the striking arm and the inserter to move the striking arm and the inserter in a second direction corresponding to the first direction.

12. The apparatus as recited in claim 11, wherein the first end of the striking arm includes at least one hook, the at least one hook being configured to engage a post defined on the inserter.

13. The apparatus as recited in claim 11, wherein the connector on the second end of the striking arm includes a substantially spherical ball.

14. The apparatus as recited in claim 13, wherein the attachment portion on the slap hammer is configured to engage the substantially spherical ball.

15. The apparatus as recited in claim 11, wherein the striking arm has a substantially arcuate configuration between the first end and the second end.

16. The apparatus as recited in claim 11, wherein the movable portion includes a first threaded portion defined on an external surface thereof, the first threaded portion being defined proximate the intermediate position.

17. The apparatus as recited in claim 16, further comprising a tightening knob provided over the first threaded portion of the movable portion, the tightening knob including a second threaded portion, the second threaded portion engaging the first threaded portion, wherein rotation of the tightening knob moves the movable portion of the inserter relative to the non-movable portion.

18. The apparatus as recited in claim 11, wherein the securing device includes a projecting portion having a selected shape configured to be received in a receiving portion of a spinal implant.

19. The apparatus as recited in claim 11, wherein the securing device includes a first cam defined at the distal end of the inserter, the first cam being configured to fit into a corresponding slot in a spinal implant.

20. The apparatus as recited in claim 11, in combination with a substantially B-shaped implant.

* * * * *

UNITED STATES PATENT AND TRADEMARK OFFICE
CERTIFICATE OF CORRECTION

PATENT NO. : 10,219,917 B2
APPLICATION NO. : 14/930994
DATED : March 5, 2019
INVENTOR(S) : Jonathan M. Dewey Page 1 of 1

It is certified that error appears in the above-identified patent and that said Letters Patent is hereby corrected as shown below:

In the Specification

In Column 5, Line 18, delete "d" and insert -- d1 --, therefor.

Signed and Sealed this
Second Day of July, 2019

Andrei Iancu
*Director of the United States Patent and Trademark Office*